United States Patent [19]

Ohnishi

[11] Patent Number: 5,421,813
[45] Date of Patent: Jun. 6, 1995

[54] METHOD FOR CLEANING HUMOR REPLACING CIRCUIT, JOINT FOR FORMING THE CIRCUIT, AND MEDICAL INSTRUMENT CONTAINER, FOR USE IN MEDICAL TREATMENT

[75] Inventor: Michikazu Ohnishi, Hyogo, Japan

[73] Assignee: Kanegafuchi Kagaku Kogyo Kabushiki Kaisha, Osaka, Japan

[21] Appl. No.: 24,773

[22] Filed: Mar. 2, 1993

[30] Foreign Application Priority Data

Mar. 3, 1992 [JP] Japan .................. 4-097489
Mar. 3, 1992 [JP] Japan .................. 4-097490

[51] Int. Cl.⁶ .................................. A61M 37/00
[52] U.S. Cl. .......................... 604/4; 137/599.1; 604/29; 210/646
[58] Field of Search ................ 604/4-6, 604/29; 137/599.1, 601; 128/DIG. 13; 210/646, 137, 805, 140, 929; 422/36, 37, 292; 134/22.17, 22.18, 26

[56] References Cited

U.S. PATENT DOCUMENTS

| | | | |
|---|---|---|---|
| 3,187,570 | 6/1965 | Mueller | 137/599.1 |
| 3,256,735 | 6/1966 | Smith | 137/599.1 |
| 4,122,010 | 10/1978 | Riede | 210/90 |
| 4,158,034 | 6/1979 | Riede | 422/36 |
| 4,728,496 | 3/1988 | Petersen | 422/1 |

FOREIGN PATENT DOCUMENTS 0270794 10/1987 European Pat. Off. .
2559241 12/1975 Germany .
3836399A1 5/1990 Germany .

OTHER PUBLICATIONS

European Search Report dated Nov. 30, 1993.

*Primary Examiner*—Randall L. Green
*Assistant Examiner*—Rob Clarke
*Attorney, Agent, or Firm*—Armstrong, Westerman, Hattori, McLeland & Naughton

[57] ABSTRACT

This invention is directed to a method for cleaning a humor replacing circuit, in its entirety, by simply switching valves of joints connected to end portions of ducts which interconnect medical instruments (such as, a membrane type plasma separator, a selective plasma component absorber or a membrane filter); a joint which can be readily replaced and connected to the medical instruments; and a medical instrument container. The method for cleaning, the joint, and the medical instrument container are used in medical treatment (such as, dialysis or plasma replacing therapy).

4 Claims, 6 Drawing Sheets

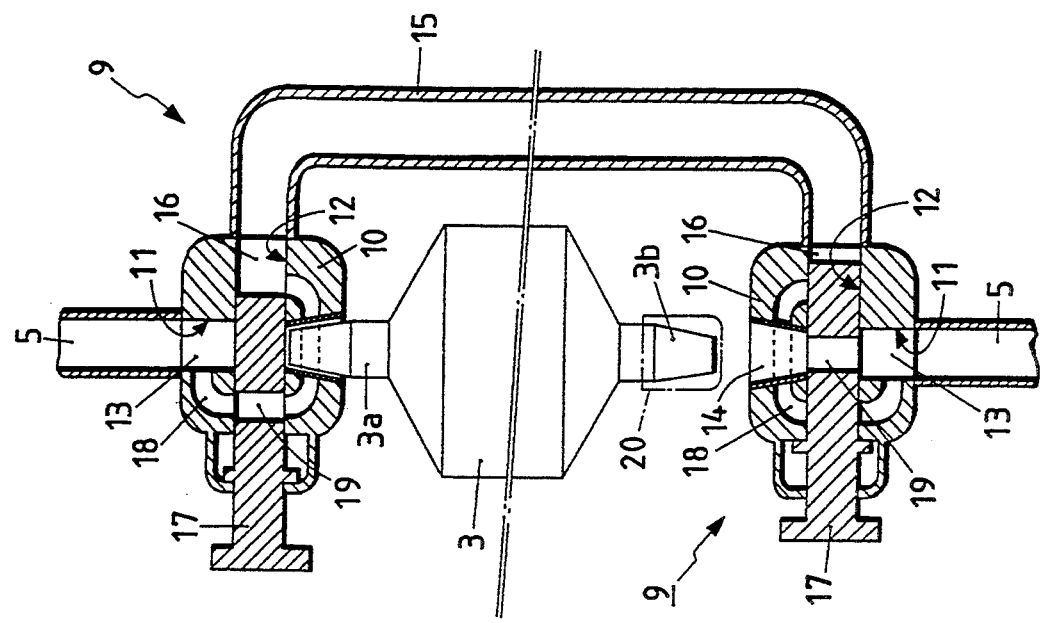
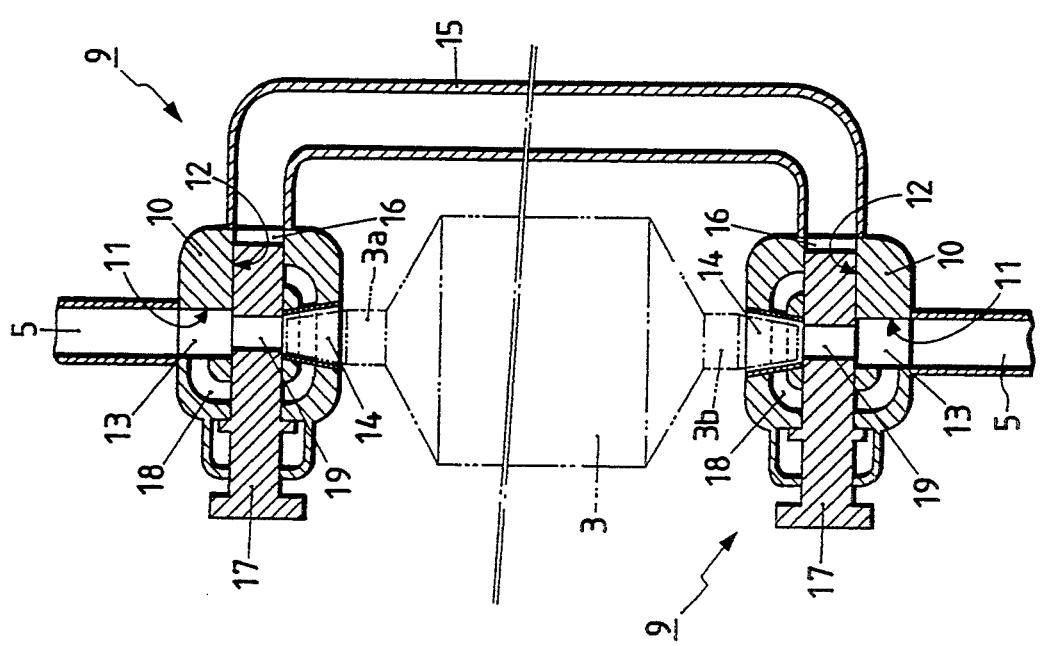

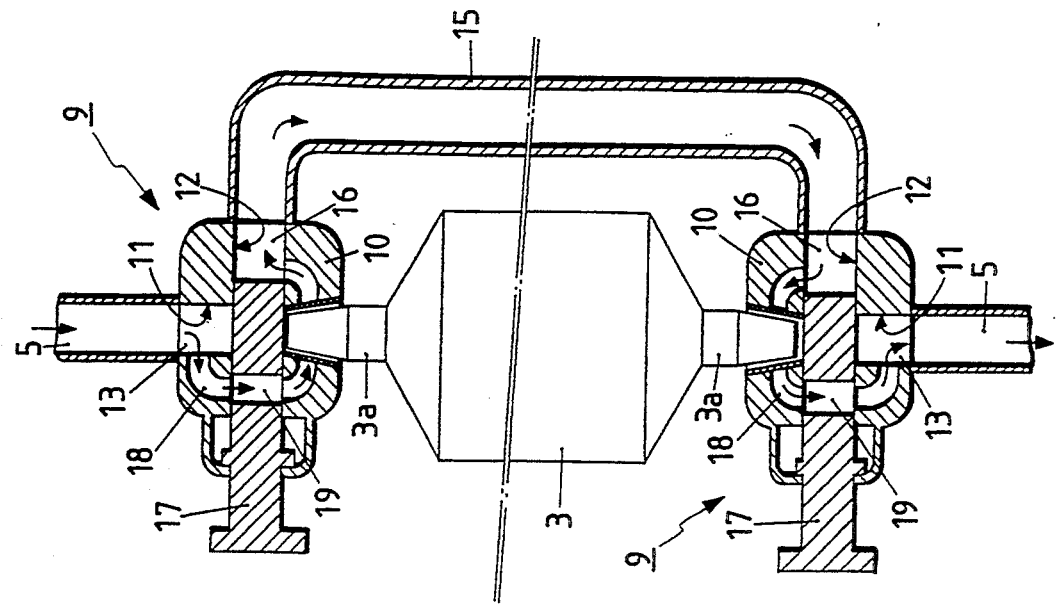
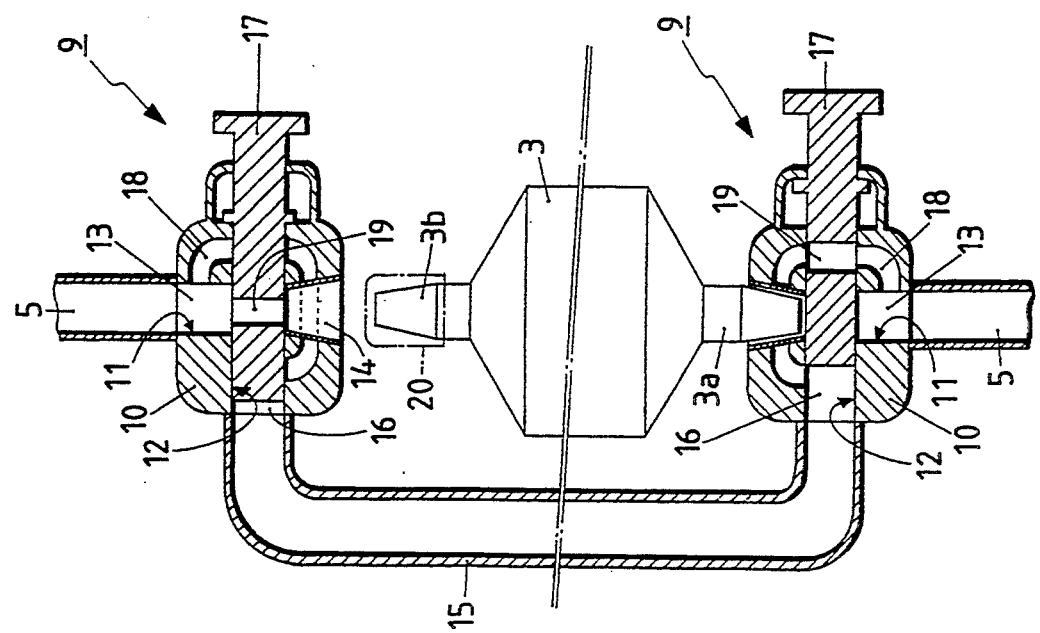

METHOD FOR CLEANING HUMOR REPLACING CIRCUIT, JOINT FOR FORMING THE CIRCUIT, AND MEDICAL INSTRUMENT CONTAINER, FOR USE IN MEDICAL TREATMENT

BACKGROUND OF THE INVENTION

1. Field of the Invention

This invention generally relates to: a method for cleaning a humor replacing circuit formed by interconnecting medical instruments (such as, a membrane type plasma separator, a selective plasma component absorber, and a membrane filter); a joint for forming the circuit; and a medical instrument container used in the circuit. The method, the joint, and the medical instrument container are used for medical treatment (such as, dialysis or plasma replacing therapy).

2. Description of the Relevant Art

As shown in FIG. 1, a humor replacing circuit 1 used for medical treatment (such as, dialysis or plasma replacing therapy) is usually formed by interconnecting medical instruments (such as, a membrane type plasma separator 2, a selective plasma component absorber 3, and a membrane filter 4) through ducts 5. After the entire humor replacing circuit 1 has been cleaned, a desired treatment (such as, dialysis or plasma replacing therapy) is effected. In this circuit, it is essential to shut bubbles out while the circuit is being assembled and cleaned.

Two methods have thus been made available so as to provide a humor replacing circuit 1, while preventing undesired bubbles from entering.

One of the methods repeats the sequential operation of connecting a duct 5 to a medical instrument, while releasing air and cleaning, one by one, so as to complete the assembling of all the ducts and the medical instruments.

The other method employs dummy tubes 6, as shown in FIGS. 2 through 5. This method includes the steps of: interconnecting the ends of ducts 5, between which a medical instrument is to be interposed, through a dummy tube 6 to form a circuit whose components communicate with one another; air-releasing and cleaning the entire circuit outright; and then replacing the dummy tubes 6 with medical instruments, while being careful not to have bubbles enter the circuit.

FIGS. 2 to 5 show a conventional method of replacing the selective plasma component absorber 3 with a dummy tube 6. First, as shown in FIG. 2, the ends of ducts 5 interposing the dummy tube 6 are clamped by forceps 7.

Then, as shown in FIG. 3, one of the ducts 5 is connected to an outlet port 3b by insertion with the absorber 3 being inverted. If the outlet port 3b is not filled with a filling solution (such as, a sodium citrate aqueous solution), the connecting operation is performed by replenishing physiological saline by an injector 8, while keeping bubbles from entering.

As shown in FIG. 4, the duct 5 is inserted to an inlet port 3a for connection, while inverting the absorber 3 back to the normal position. Physiological solution may similarly be replenished, if necessary.

As the final step, the forceps is taken out to remove clamping, as shown in FIG. 5, in order to complete the operation of replacing the dummy tube 6 with the absorber 3.

However, the method of sequentially assembling the humor replacing circuit, while releasing air and cleaning the circuit components one by one involves the operation of connecting the ducts one by one while being careful not to have bubbles enter the circuit; thereby, entailing extremely cumbersome and careful work since there are many points of connection in the above-described conventional method. As a result, the burden of the operator becomes intolerable which results in connecting errors or the like. These are, consequently, the drawbacks and shortcomings of the conventional method.

On the other hand, the method employing the dummy tubes 6 allows the entire circuit to be cleaned outright, but involves the operation of connecting the dummy tubes 6 to the predetermined portions of the ducts 5; thus, still requiring complicated preparatory work which is also a shortcoming.

This invention is therefore provided in order to overcome the above-described problems. Accordingly, the object of this invention is to provide: a method of cleaning an entire humor replacing circuit by simply operating the switching valves of the joints connected to the ends of the ducts; a joint that can be readily replaced and connected to medical instruments; and a medical instrument container.

In order to achieve the above objects, a first aspect of this invention is applied to a method of cleaning a humor replacing circuit formed by interconnecting medical instruments (such as, a membrane type plasma separator, a selective plasma component absorber, and a membrane filter). The method includes the steps of: assembling a cleaning circuit by connecting a joint having a two-way switching valve body to an end of a duct for interconnecting the medical instruments; connecting a pair of connected joints by a bypass so that the joints confront each other; interposing a medical instrument (such as, the membrane type plasma separator or the selective plasma component absorber) between the confronting joints, and switching the two-way switching valve body to such a position so as to allow the bypass to communicate with the joints; carrying out a first cleaning of the entire circuit under such a condition; and carrying out a second cleaning and priming by switching the two-way switching valve body to the other position.

A second aspect of this invention is directed to a method that includes the steps of: preparing a joint having connecting ends of an inlet and an outlet of a medical instrument, connecting ends of two ducts for interconnecting the medical instruments, a two-way switching valve body, and a bypass capable of communicating with the two ducts; switching the two-way switching valve body to one position to cause the two ducts to communicate with each other through the bypass; carrying out a first cleaning of the entire circuit under this condition; switching the two-way switching valve body to the other position to cause the two ducts to communicate with the medical instrument; and carrying out a second cleaning and priming under this condition.

A third aspect of the invention is directed to a joint for a humor replacing circuit for interconnecting a medical instrument (such as, a membrane type plasma separator, a selective plasma component absorber or a membrane filter). A body of the joint includes: a connecting end for connecting a medical instrument; a connecting end for inserting an inlet or an outlet of the medical instrument; and a connecting end of a bypass for interconnecting a pair of joints corresponding to the inlet and the outlet of the medical instrument. The joint body has a two-way switching valve body that is slidable therewithin, the two-way switching valve body allowing the three connecting ends inside the joint body to be switched.

A fourth aspect of this invention is directed to a joint having a body which includes: a two-way switching valve body arranged so as to be slidable therewithin; connecting ends for inserting an inlet and an outlet of a medical instrument; connecting ends of two ducts for interconnecting the medical instruments; and a bypass capable of communicating with the two ducts through the two-way switching valve body.

A fifth aspect of this invention is directed to a medical instrument container for accommodating a medical instrument (such as, a membrane type plasma separator, a selective plasma component absorber or a membrane filter) used in a humor replacing circuit for medical treatment (such as, dialysis or plasma replacing therapy). The container is arranged so that the horizontal level of the container is as high as that of an inlet and an outlet of the medical instrument.

This invention includes the connection of a joint having a two-way switching valve body to the end of a duct that interconnects medical instruments, and the further interconnecting of two such connected joints respectively corresponding to the inlet and the outlet of a medical instrument through a bypass.

Therefore, by switching the switching valve body, the ducts communicate with each other through the bypass interconnecting the joints; thereby, allowing the entire humor replacing circuit to be cleaned. In addition, a desired humor replacing circuit can be conveniently formed by merely inserting a medical instrument to the connecting ends of each pair of joints.

Another aspect of this invention is directed to the connection of two ducts and the inlet and the outlet of a single medical instrument to a joint having a two-way switching valve body and a bypass, the two ducts interconnecting medical instruments. By setting the two-way switching valve body to one of the positions, the two ducts can communicate with each other through the bypass; thereby, allowing all the ducts belonging to the humor replacing circuit to be subjected to a first cleaning.

Further, by setting the two-way switching valve body to the other position, the two ducts can be connected to the inlet and the outlet of the medical instrument, respectively; thereby, allowing the entire circuit throughout the medical instruments to be subjected to second cleaning and priming.

These and other features of the invention will be understood upon reading of the following description along with the drawings. It is noted that the same reference numbers used in the above-described conventional method and apparatus are used for designating various parts or components of this invention.

BRIEF DESCRIPTION OF THE DRAWINGS

FIG. 6 is a longitudinal sectional view showing joints of this invention;

FIG. 7 is a longitudinal sectional view showing a method for interconnecting the joints and the inlet of an absorber of this invention;

FIG. 8 is a longitudinal sectional view showing a method for interconnecting the joints and the outlet of the absorber of this invention;

FIG. 9 is a longitudinal sectional view showing the joints and the absorber of this invention at a state for a first time cleaning;

DETAILED DESCRIPTION OF THE PREFERRED EMBODIMENTS

Figure 1:
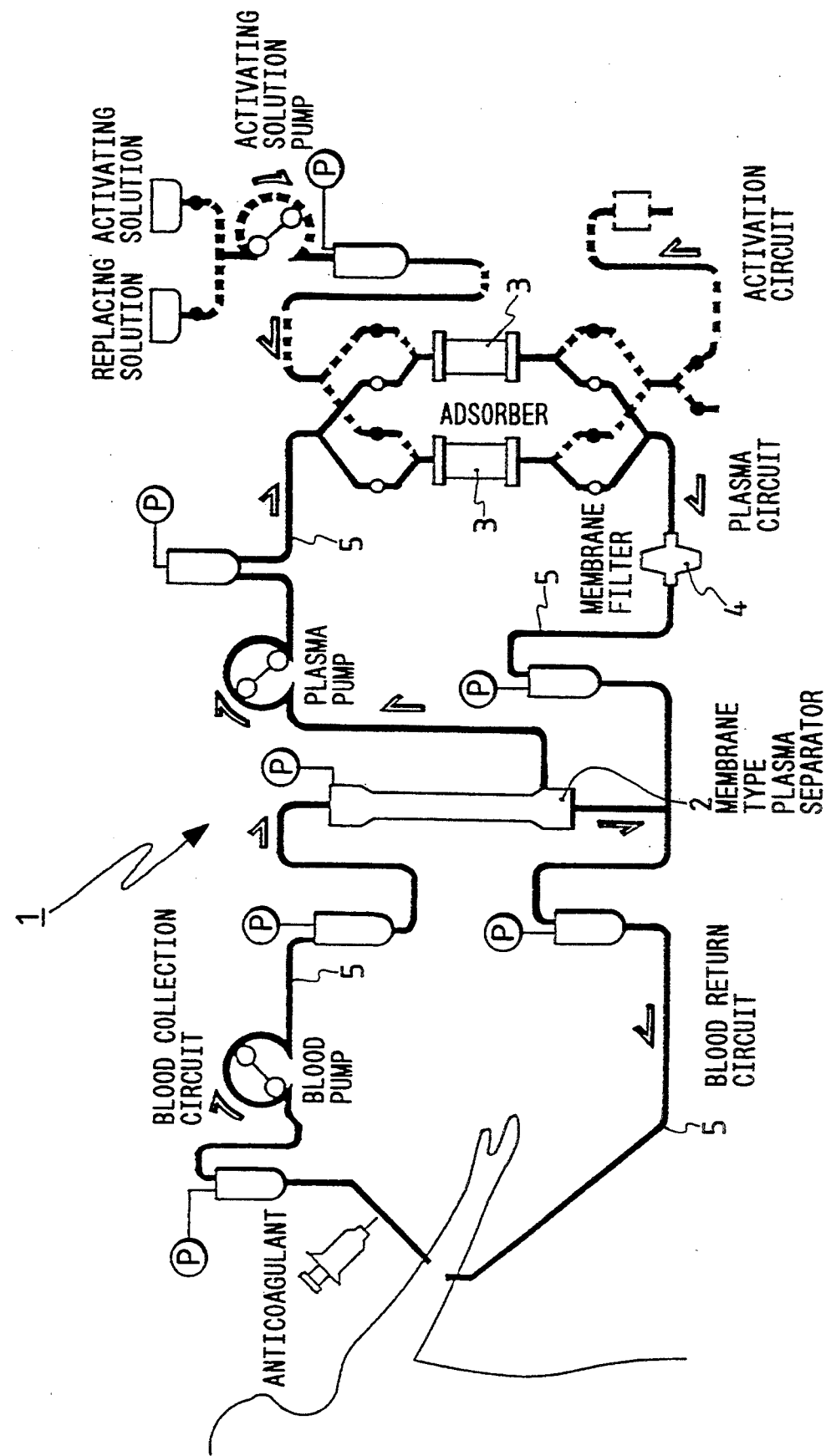
FIG. 1 is a front view showing a conventional humor replacing circuit.
Figure 5:
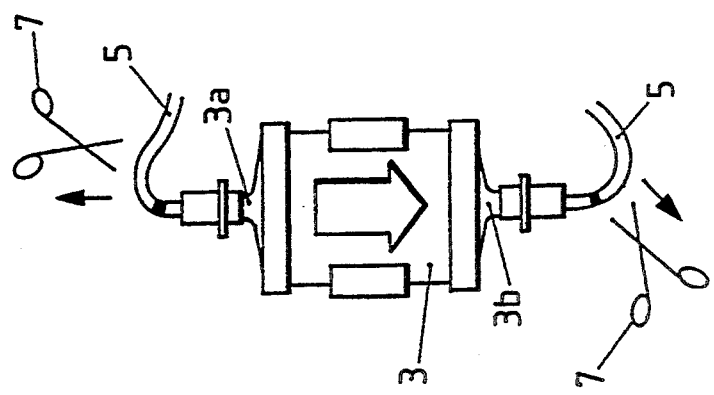
FIG. 5 is a front view showing a state in which the duct and the absorber of a conventional type have been completely interconnected.
Figure 4:
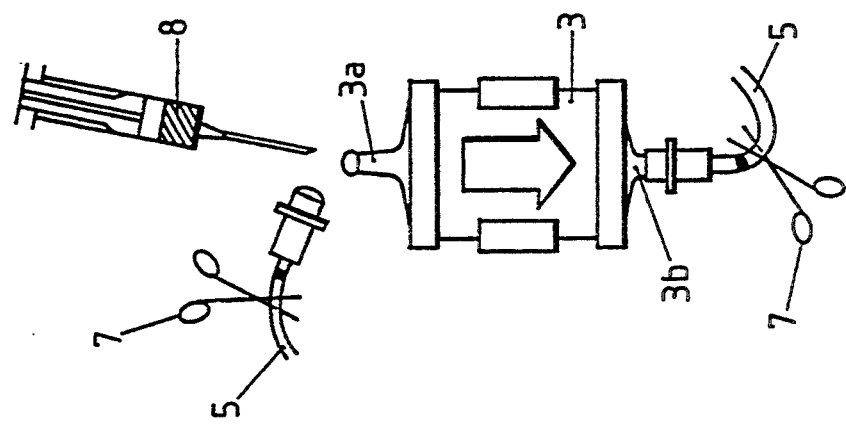
FIG. 4 is a front view showing a method for interconnecting a duct and the inlet of the absorber of a conventional type.
Figure 3:
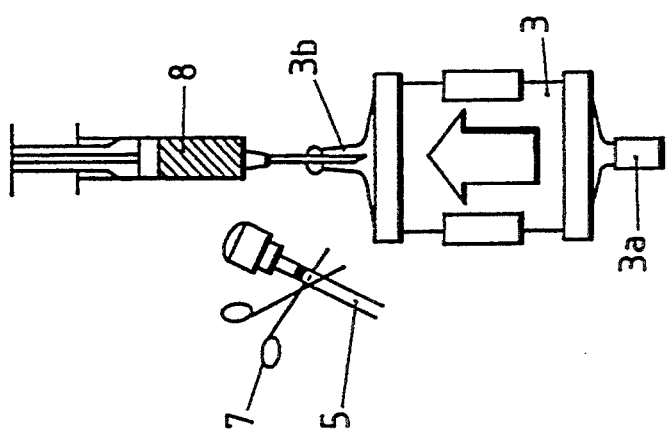
FIG. 3 is a front view showing a method for interconnecting a duct and the outlet of an absorber of conventional type.
Figure 2:
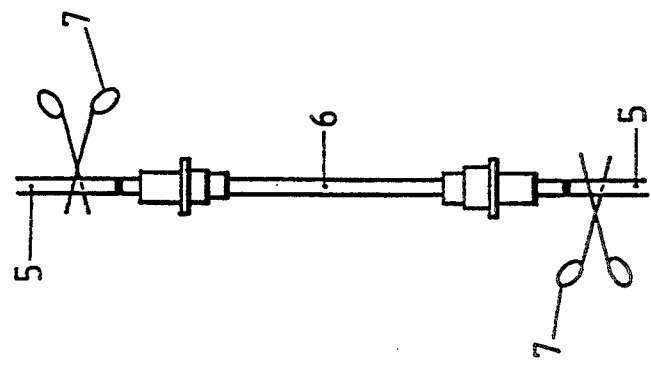
FIG. 2 is a front view showing a method for interconnecting ducts and a dummy tube of a conventional type.

FIGS. 6 through 10 are partially enlarged longitudinal sectional views showing a cleaning method of this invention and the steps of a method for replacing and interconnecting medical instruments. As shown in these figures, each of joints 9 is connected to an end of a duct 5. A humor replacing circuit 1 is formed by interconnecting each medical instrument to such a joint 9.

Each joint 9 has through-holes 11 and 12, both intersecting orthogonally to each other in the vertical and horizontal directions with respect to a joint body 10. The upper and lower ends of the through-hole 11 serve as connecting ends 13, 14, the connecting end 13 serving as an end for connecting a duct 5 and the connecting end 14 serving as an end for connecting a medical instrument (a selective plasma component absorber in this embodiment) 3. One end of the through-hole 12 serves as a connecting end 16 of a bypass 15 that interconnects the pair of confronting joints 9, 9, whereas the other end thereof serves as an end for attaching a two-way switching valve body 17. Further, a communicating path 18 that allows the connecting end 13 connected to the duct 5 and the connecting end 16 of the bypass 15 to communicate are provided inside the joint body 10.

Since a port 19 is arranged in the switching valve body 17 so as to extend therethrough in a vertical direction, a connection in which the connecting end 13 on the duct 5 side communicates with the connecting end 14 on the absorber 3 side can be switched to a connection in which the connecting end 13 on the duct 5 side communicates with the connecting end 16 on the bypass 15 side, where necessary. Caps 20 are placed on an inlet 3a and an outlet 3b of the absorber 3 before the absorber 3 is connected so that a filling solution (such as, a sodium citrate aqueous solution) inside the absorber will not be lost.

A method for cleaning the humor replacing circuit 1 in which the constructed joints 9 are connected to the ends of the ducts 5, a procedure for replacing and interconnecting the medical instruments, and a medical treatment technique will be described hereinafter.

As shown in FIG. 6, with the port 19 of the switching valve body 17 of the joint 9 corresponding to the inlet 3a of the absorber 3 communicating with the through-hole 11 and the duct 5, the cap 20 on the inlet 3a of the absorber 3 is taken out, and the inlet 3a is inserted into the connecting end 14 of the joint body 10. The switching valve body 17 is moved leftward as viewed in FIG. 6 under this condition so that the through-hole 11 is shut off as shown in FIG. 7. Then, as shown in FIG. 8, the absorber 3 and the pair of confronting joints 9, 9 are turned upside down. Then, the cap 20 on the outlet 3b of the absorber 3 is taken out, and the outlet 3b is inserted into the connecting end 14 of the joint body 10 of the joint 9 corresponding to the outlet 3b with the port 19 thereof communicating with the through-hole 11 and the duct 5. Then, the switching valve body 17 of the joint 9 corresponding to the outlet 3b of the absorber 3 is operated so that the through-hole 11 is shut off.

As shown in FIG. 9, the absorber 3 and the joints 9, 9 are again inverted thereafter to place them back into a regular position. A similar operation will be performed at respective medical instrument connecting positions. The operation of replacing and interconnecting the medical instruments, as well as the assembling of the humor replacing circuit 1, is thus completed.

With the operation for replacing and interconnecting the medical instruments completed in this manner, and with the switching valve body 17 of the pair of joints 9, 9 connected to the inlet and the outlet of each medical instrument positioned as shown in FIG. 9, the humor replacing circuit 1 communicates with all the ducts 5 and the bypasses 15 of the respective medical instruments through the connecting ends 13, the communicating paths 18, and the connecting ends 16 of the joint bodies 10. Thus, the entire humor replacing circuit 1 can be readily cleaned. This cleaning method is extremely simple and convenient with the switching of the switching valve body 17 being the only operation required as a preparation. This cleaning, carried out to clean the entire ducts, is called "first cleaning".

Figure 10:
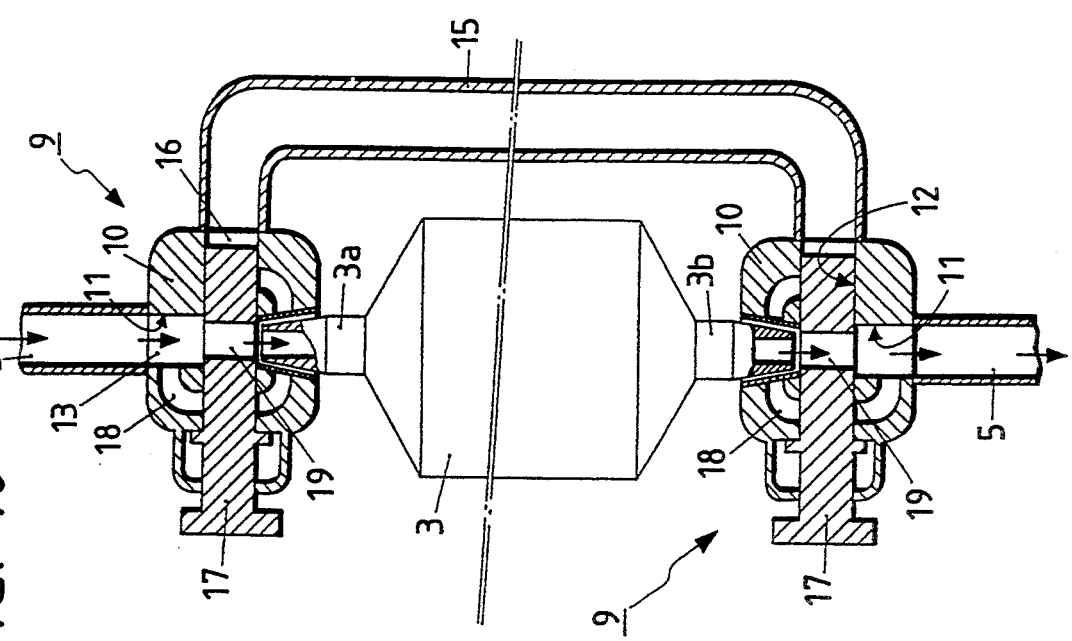
FIG. 10 is a longitudinal sectional view showing the joints and the absorber of this invention for a second time cleaning and priming.

When the first cleaning has been completed, the switching valve bodies 17 of the respective joints 9 are moved rightward from the state as shown in FIG. 9 to place each medical instrument in a state as shown in FIG. 10. Thus, the ducts 5 communicate with each other through the through-hole 11 of each joint body 10 and the port 19 of each switching valve body 17; thereby, allowing a second cleaning to be started, the second cleaning being carried out by flushing through each medical instrument.

Upon the termination of the second cleaning, priming is started under the same condition. Priming means the operation of substituting a cleaning solution remaining in the humor replacing circuit 1 for a priming solution prepared by adding heparin to a Ringer's solution or the like at a predetermined ratio. Upon the termination of priming, medical treatment (such as, dialysis and plasma replacing therapy) is given.

As described above, this embodiment allows the operation of cleaning the humor replacing circuit 1 and replacing and interconnecting the medical instruments, as well as the desired medical treatment, to be performed with substantial simplicity and ease.

It is also noted that this invention is not limited to the above-described embodiment. The connecting ends 13, 14, 16 of the joint body 10 may be provided at different positions and the shape of the communicating path 18 may also be modified where appropriate. Further, the organization of the humor replacing circuit 1 and the types of medical instruments may be selected in accordance with a desired medical treatment.

Figure 11:
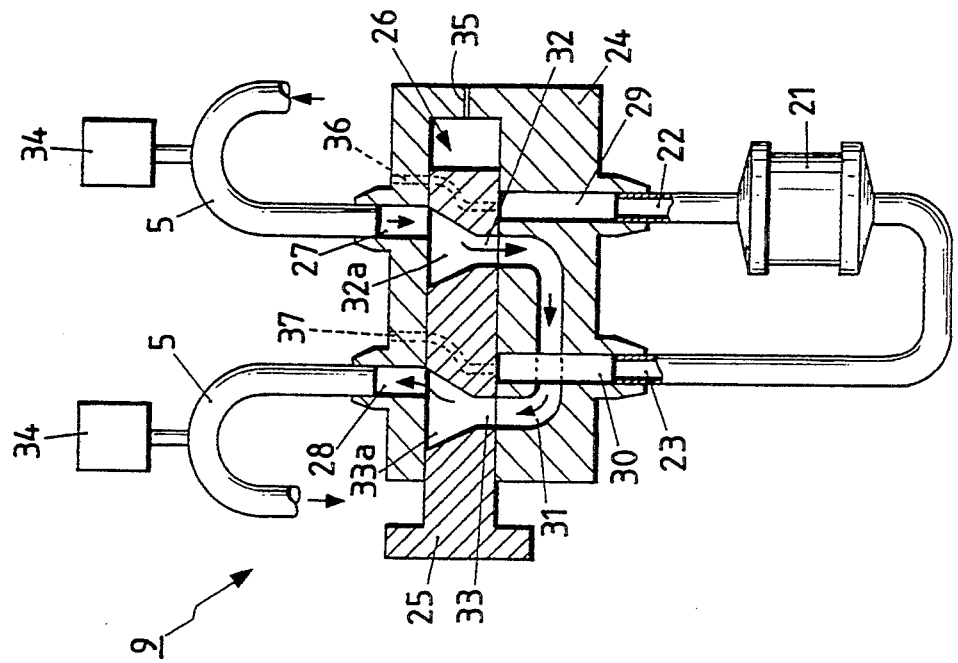
FIG. 11 is a longitudinal sectional view showing the joints and the absorber of this invention for a first time cleaning.
Figure 12:
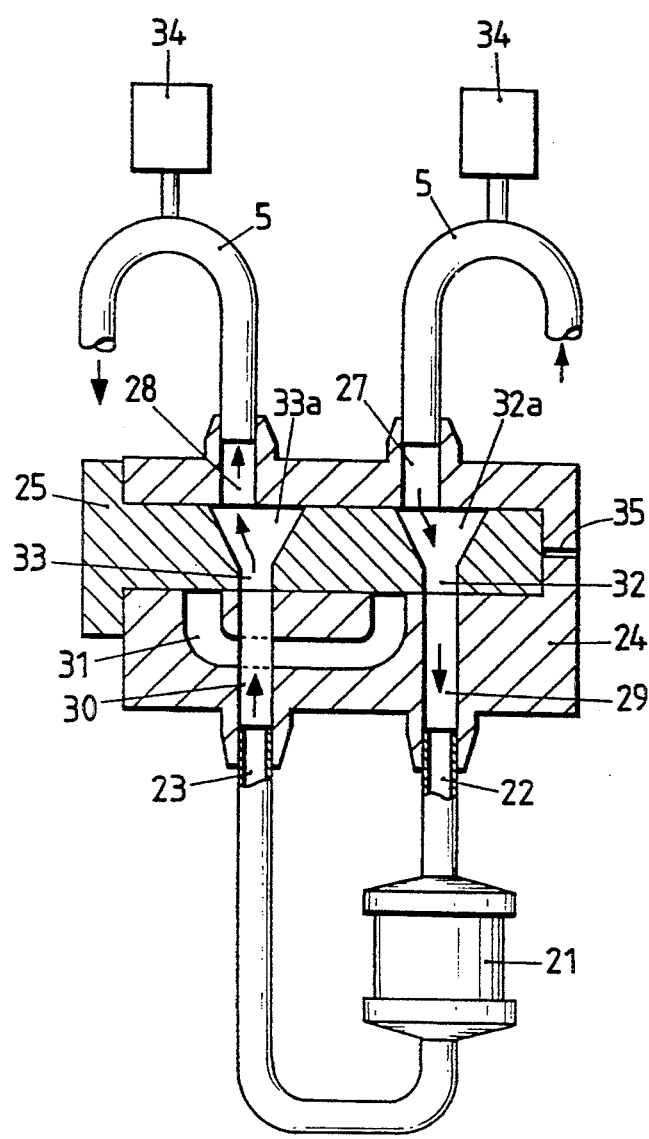
FIG. 12 is a longitudinal sectional view showing the joints and the absorber of this invention for a second time cleaning.

FIGS. 11 and 12 show another embodiment of this invention. FIG. 11 is a longitudinal sectional view showing a state of the first cleaning with the medical instrument 21 (the selective plasma component absorber in this embodiment) and the ducts 5 connected to a joint 9. FIG. 12 is a longitudinal sectional view showing a state of the second cleaning. As shown in these figures, this embodiment includes the connection of the ends of the ducts 5 to the upper side of the joint 9 to form a humor replacing circuit 1 which is constructed by connecting medical instruments through the joint and the ducts 5. On the lower side of the joint 9 are an inlet 22 and an outlet 23 of the absorber 21.

An inserting hole 26 of a two-way switching valve 25 is provided in a joint body 24 of the joint 9. The valve body 25 is fitted into the inserting hole 26 so as to be slidable in a horizontal direction. On the upper side of the joint body 24 are an inlet 27 and an outlet 28 for connecting the ends of two ducts 5. The inlet 27 and the outlet 28 communicate with the inserting hole 26 of the valve body 25. On the lower side of the joint body 24 are connecting ends 29, 30 for connecting the inlet and the outlet of a medical instrument. These connecting ends 29, 30 also communicate with the inserting hole 26 of the valve body 25. Further, the joint body 24 has a bypass 31 that is designed not to communicate with the inlet 27 and the outlet 28 nor with the connecting ends 29, 30, but to communicate with the inlet 27 and the outlet 28 when the valve body 25 is slid to a certain position inside the inserting hole 26.

Moreover, the switching valve body 25 has two communicating paths 32, 33 passing through a vertical direction. The communicating paths 32, 33 have enlarged ports 32a, 33a on the upper sides thereof, respectively. The ports 32a, 33a are so designed that they communicate with the inlet 27 and the outlet 28 at all times without being affected by the position to which the switching valve body 25 is slid. The ports 32a, 33a may be bifurcated as long as they communicate with the inlet 27 and the outlet 28 depending on the position of the switching valve body 25. On the other hand, the lower side of the communicating paths 32, 33 are designed to communicate with the connecting ends 29, 30 or with the bypass 31, depending on the position of the switching valve body 25.

Further, the absorber 21 is connected to the connecting ends 29, 30 of the joint body 24 through the inlet and the outlet thereof implemented by two hoses. One of the hoses is short and the other is long so that the horizontal level of the inlet 22 end is equal to that of the outlet 23 end. In FIGS. 11 and 12, reference numeral 34 designates a gas-liquid separator, disposed along the duct 5, for driving bubbles out; and reference numeral 35 designates an air hole disposed on the right end of the inserting hole 26. Replenishing solution paths 36, 37 may be arranged at positions shown by broken lines in FIG. 11 so that physiological saline may be replenished, before the first cleaning, to be substituted for air inside the connecting ends 29, 30.

A method for cleaning the thus constructed humor replacing circuit, a procedure for replacing and interconnecting the medical instruments, as well as a medical treatment technique, will be described next.

As shown in FIG. 12, the ends of the ducts 5, 5 for causing medical instruments to communicate with one another are connected to the inlet 27 and the outlet 28 of the joint body 24 with the switching valve body 25 positioned at the rightmost end. The inlet 22 and the outlet 23 of the absorber 21 are fitted into the connecting ends 29, 30. Then, the switching valve body 25 is moved leftward, as shown in FIG. 11, so that the port 32a of the switching valve body 25 communicates with the inlet 27 of the joint body 24 and the lower end of the communicating path 32 communicates with one end of the bypass 31; whereas, the port 33a thereof communicates with the outlet 28 and the lower end of the communicating path 33 communicates with the other end of the bypass 31.

Thus, all the ducts 5 of the humor replacing circuit 1 communicate with the inlet 27, the outlet 28 of each joint 9, the communicating paths 32, 33 of the switching valve body 25 corresponding to the joint 9, and the bypass 31. As a result of this structural arrangement, all the ducts 5 of the humor replacing circuit 1 can be directly cleaned. In addition, what is required as a preparation for such a cleaning is only the switching of the switching valve body 25. Thus, cleaning is extremely simple and convenient. Such cleaning is called "first cleaning."

Upon completion of the first cleaning, the switching valve body 25 of the joint 9 is moved rightward from the state, as shown in FIG. 11, to be switched to another state, as shown in FIG. 12. Thus, the inlet 27 of the joint body 24 communicates with the inlet 22 of the absorber 21 through the communicating path 32 of the switching valve body 25; whereas, the outlet 28 communicates with the outlet 23 of the absorber 21 through the communicating path 33 of the switching valve body 25. That is, the ducts 5 of the humor replacing circuit 1 communicates with the corresponding medical instrument.

Second cleaning is started thereafter under the condition, as shown in FIG. 12. Upon the termination of the second cleaning, priming is started under the same condition. Priming is the operation of substituting the cleaning solution remaining inside the humor replacing circuit 1 for a priming solution prepared by adding heparin to Ringer's solution at a predetermined ratio. After priming has been done, predetermined medical treatment (such as, dialysis or plasma replacing therapy) is given.

In this embodiment, not only can the operation of cleaning the humor replacing circuit, and of replacing and interconnecting the medical instruments be performed at substantial simplicity and ease, but also the desired medical treatment can be similarly given at substantial simplicity and ease.

Figure 13:
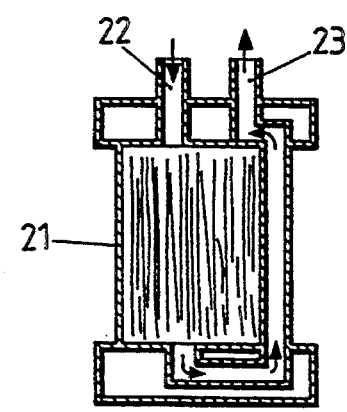
FIG. 13 is a longitudinal sectional view showing an absorber which is another embodiment of this invention.
Figure 14:
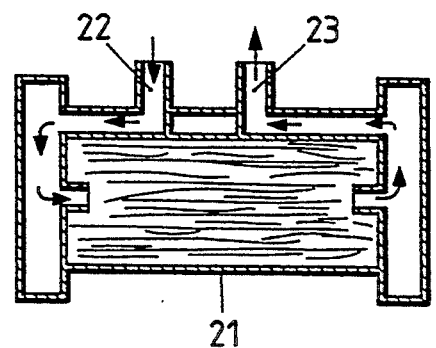
FIG. 14 is a longitudinal sectional view showing an absorber which is still another embodiment of this invention.

It is also noted that the application of this invention is not limited to the above-described embodiment. For example, with respect to the container for containing the absorber 21, which in this embodiment is a medical instrument, the absorbers shown in FIGS. 13, 14 may be employed in addition to the absorbers shown in FIGS. 11 and 12. The absorber shown in FIG. 13 is a vertical type, while the inlet 22 and the outlet 23 are arranged at the same horizontal level on the upper side of the container. The absorber shown in FIG. 14 is a horizontal type, while the inlet 22 and the outlet 23 are arranged on the same horizontal level on the upper side of the container. Other aspects of the construction are the same as those shown in FIGS. 11 and 12.

The structural arrangement of the humor replacing circuit 1, the types of the medical instruments, and the like, may be selected in accordance with a desired medical treatment.

Further, the embodiment of the joint 9 shown in FIG. 11 may likely leave air in the space between the absorber 21 of the joint body 24 and the connecting ends 29, 30 during the first cleaning. However, the air passes along the ducts 5 through the communicating paths 32, 33, as well as, the inlet 27 and the outlet 28 due to the buoyancy thereof when, upon the termination of the first cleaning, the switching valve body 25 is switched by moving the switching valve body rightward, as viewed in FIG. 11, and when the cleaning solution, immediately before second cleaning, stays stationary in the ducts 5. The air is thereafter substituted for a portion of the cleaning solution staying in the upper portion of each duct 5. Since the air, having risen along the ducts 5, is then received by the gas-liquid separators 34, no problem will arise therefrom.

As another measure to handle such air, the joint body 24 shown in FIG. 11 may be inverted and physiological saline may be replenished in the connecting ends 29, 30 immediately before connecting the absorber 21 prior to the start of the first cleaning.

As described above, the invention is designed not only to connect the joint having the two-way switching valve body to the end of the duct that interconnects medical instruments (such as, a membrane type plasma separator and a selective plasma component absorber), but also to connect a pair of such connected joints respectively corresponding to the inlet and the outlet of a medical instrument through the bypass in forming the humor replacing circuit used in the medical treatment (such as, dialysis or plasma replacing therapy).

Further, this invention includes the method step of connecting the two ducts that interconnect medical instruments and the inlet and the outlet of a single medical instrument to the joint having the two-way switching valve body and the bypass. By operating the two-way switching valve body to one of the positions, the two ducts communicate with each other through the bypass; thereby, allowing the entire humor replacing circuit to be subjected to the first cleaning.

Moreover, by switching the two-way switching valve body to the other position, the two ducts communicate with the inlet and the outlet of the medical instrument; thereby, allowing the entire circuit throughout the medical instruments to be subjected to the second cleaning and priming.

Therefore, by operating the switching valve body, the ducts of the humor replacing circuit can communicate with one another through the bypasses of the joints; thereby, allowing the entire humor replacing circuit to be cleaned outright. In other words, it is only the operation of the switching valve body that is required to clean the circuit in this invention. This is an extremely easy and simple operation.

As described above, the method for replacing and interconnecting the medical instruments does not involve replacement with dummy tubes or the like, but allows for the medical instruments to remain connected to the joints which is a method that is also extremely simple. Still further, cleaning, priming, and medical treatment can be continuously effected by simply switching the switching valve body which makes the method of this invention extremely convenient.

The above description is included to illustrate the structural arrangement and the operation of the preferred embodiments, and is not meant to limit the scope of this invention. The scope of this invention is to be limited only by the following claims. From the above discussion, many variations are apparent to one skilled in the art which would yet be encompassed by the spirit and scope of this invention.

What is claimed is:

1. A method for cleaning a humor replacing circuit formed by interconnecting at least one medical instrument, the method comprising the steps of:

assembling a cleaning circuit, wherein the step of the circuit assembling comprises the steps of connecting a joint having a two-way switching valve body to an end of a duct for interconnecting the medical instrument, connecting a pair of connected joints by a bypass so that the joints confront each other, interposing a medical instrument between the confronting joints, said medical instrument being one of the membrane type plasma separator and the selective plasma component absorber, and switching the two-way switching valve body to a position so as to allow the joints to communicate with one of: (1) the end of the duct for interconnecting the medical instrument and (2) the end of the duct for interconnecting the bypass, wherein the step of switching the two-way switching valve body includes the step of linearly sliding the two-way switching valve body towards or away from one of the pair of connected joints of the bypass;

carrying out a first cleaning of the entire circuit; and carrying out a second cleaning and priming by switching the two-way switching valve body to another position.

2. A joint for a humor replacing circuit for interconnecting a medical instrument, wherein the medical instrument is one of a membrane type plasma separator, a selective plasma component absorber, and a membrane filter, the joint comprising:

a first connecting end portion means for connecting an inlet of the medical instrument;

a second connecting end portion means for inserting an outlet of the medical instrument;

a third connecting end portion means of a bypass for interconnecting a pair of joints corresponding to the inlet and the outlet of the medical instrument; and a joint body having a two-way switching valve body arranged so as to be linearly slidable therewithin, the two-way switching valve body allowing the first, second and third connecting end portion means inside the joint body to be switched for allowing connection of one of: (1) the first and second connecting end portion means with the inlet and outlet of the medical instrument, respectively; and (2) the third connecting end portion means of the bypass with the pair of joints at the inlet and outlet of the medical instrument, wherein the two-way switching valve body linearly slides towards or away from the third connecting end portion means of the bypass.

3. A method for cleaning a humor replacing circuit formed by interconnecting at least one medical instrument, wherein the medical instrument is one of a membrane type plasma separator, a selective plasma component absorber, and a membrane filter, the method comprising the steps of:

preparing a joint having connecting end portions of an inlet and an outlet of the medical instrument, connecting ends of two ducts for interconnecting the medical instrument, a two-way switching valve body, and a bypass capable of communicating with the two ducts;

first switching the two-way switching valve body to one position to cause the two ducts to communicate with each other through the bypass, wherein the step of first switching comprises the step of linearly sliding the two-way switching valve body away from a connecting end portion of the bypass;

carrying out a first cleaning of the entire circuit;

second switching the two-way switching valve body to another position to cause the two ducts to communicate with the medical instrument, wherein the step of second switching comprises the step of linearly sliding the two-way switching valve body towards another connecting end portion of the bypass; and carrying out a second cleaning and priming under this condition.

4. A joint for a humor replacing circuit for interconnecting at least one medical instrument, the medical instrument being one of a membrane type plasma separator, a selective plasma component absorber, and a membrane filter, the joint comprising:

a two-way switching valve body arranged slidably within a body of the joint;

connecting end portions for inserting an inlet and an outlet of the medical instrument;

connecting end portions of two ducts for interconnecting the medical instrument; and a bypass capable of communicating with the two ducts through the two-way switching valve body, wherein the two-way switching valve body is linearly slidable towards or away from a connecting end portion of the bypass, and wherein the two-way switching valve connects one of: (1) the connecting end portions of the two ducts with the medical instrument, and (2) the connecting end portions of the two ducts with the bypass.

* * * * *